United States Patent
Kegelman et al.

(10) Patent No.: US 11,420,208 B2
(45) Date of Patent: *Aug. 23, 2022

(54) CAP AND INDUCTION SEAL DESIGNED TO BE OPENED BY PIERCING IN A DIAGNOSTIC ANALYZER

(71) Applicant: Siemens Healthcare Diagnostics Inc., Tarrytown, NY (US)

(72) Inventors: James W. Kegelman, Wilmington, DE (US); Joseph E. Brennan, Newark, DE (US); William E. Hudson, Bear, DE (US)

(73) Assignee: Siemens Healthcare Diagnostics Inc., Tarrytown, NY (US)

(*) Notice: Subject to any disclaimer, the term of this patent is extended or adjusted under 35 U.S.C. 154(b) by 530 days.

This patent is subject to a terminal disclaimer.

(21) Appl. No.: 16/308,794

(22) PCT Filed: Jun. 22, 2017

(86) PCT No.: PCT/US2017/038863
§ 371 (c)(1),
(2) Date: Dec. 10, 2018

(87) PCT Pub. No.: WO2018/005240
PCT Pub. Date: Jan. 4, 2018

(65) Prior Publication Data
US 2019/0308193 A1 Oct. 10, 2019

Related U.S. Application Data

(60) Provisional application No. 62/357,911, filed on Jul. 1, 2016.

(51) Int. Cl.
*B01L 3/00* (2006.01)
*B32B 15/085* (2006.01)
(Continued)

(52) U.S. Cl.
CPC ............ *B01L 3/523* (2013.01); *B29C 65/368* (2013.01); *B29C 65/3656* (2013.01);
(Continued)

(58) Field of Classification Search
CPC ............... B01L 3/5082; B01L 2300/04; B01L 2300/042; B01L 2300/044; B01L 3/523;
(Continued)

(56) References Cited

U.S. PATENT DOCUMENTS 5,230,427 A   6/1993 Betts et al.
5,381,913 A   1/1995 Peeters
(Continued)

FOREIGN PATENT DOCUMENTS

CN   101596962 A   12/2009
CN   103393539 A   11/2013
(Continued)

OTHER PUBLICATIONS

PCT International Search Report and Written Opinion dated Sep. 7, 2017 (15 Pages).
(Continued)

*Primary Examiner* — Jill A Warden
*Assistant Examiner* — Dwayne K Handy

(57) ABSTRACT

Embodiments are directed to a removable cap with a top hole and a seal with a heat induction closure for sealing an opening of a container. Advantageously, the cap and the seal do not need to be removed for a probe to access contents of the container, when used in a diagnostic analyzer, thereby eliminating operator steps of cap removal and seal peeling/perforation. Automated opening of the cap and seal combination is provided by puncturing the seal. The seal retains its opened shape required for unobstructed, non-contact probe access to contents of the container. The seal is comprised of three layers: a first polymer sealing layer capable of being (Continued)

heat-sealed to a container; an aluminum foil layer on top of the first polymer sealing layer, configured to heat seal the first layer by inductive heating; and a second polymer layer on top of the aluminum foil layer for protection.

18 Claims, 7 Drawing Sheets

(51) Int. Cl.

| | |
|---|---|
| B32B 15/09 | (2006.01) |
| B32B 15/20 | (2006.01) |
| B65D 41/34 | (2006.01) |
| B65D 41/48 | (2006.01) |
| B65D 51/20 | (2006.01) |
| B29C 65/00 | (2006.01) |
| B29C 65/36 | (2006.01) |
| G01N 1/38 | (2006.01) |
| B65D 41/04 | (2006.01) |
| G01N 33/48 | (2006.01) |
| B29C 65/56 | (2006.01) |
| B29K 705/02 | (2006.01) |
| G01N 35/04 | (2006.01) |
| B29L 31/56 | (2006.01) |
| B29L 31/00 | (2006.01) |
| G01N 35/10 | (2006.01) |

(52) U.S. Cl.
CPC .... *B29C 66/53461* (2013.01); *B29C 66/7234* (2013.01); *B29C 66/72321* (2013.01); *B29C 66/72341* (2013.01); *B29C 66/72343* (2013.01); *B32B 15/085* (2013.01); *B32B 15/09* (2013.01); *B32B 15/20* (2013.01); *B65D 41/04* (2013.01); *B65D 41/34* (2013.01); *B65D 41/48* (2013.01); *B65D 51/20* (2013.01); *G01N 1/38* (2013.01); *G01N 33/48* (2013.01); *B01L 2200/0689* (2013.01); *B01L 2200/16* (2013.01); *B01L 2300/042* (2013.01); *B01L 2300/044* (2013.01); *B01L 2300/0887* (2013.01); *B01L 2300/12* (2013.01); *B01L 2300/1816* (2013.01); *B29C 65/561* (2013.01); *B29C 66/53421* (2013.01); *B29C 66/71* (2013.01); *B29C 66/712* (2013.01); *B29C 66/73116* (2013.01); *B29K 2705/02* (2013.01); *B29L 2031/565* (2013.01); *B29L 2031/712* (2013.01); *B29L 2031/7158* (2013.01); *B32B 2307/31* (2013.01); *B32B 2435/02* (2013.01); *B65D 2251/0031* (2013.01); *B65D 2251/0078* (2013.01); *G01N 35/1079* (2013.01); *G01N 2035/0405* (2013.01)

(58) Field of Classification Search
CPC ..... B01L 3/50825; B65D 51/20; B65D 51/22; B65D 51/226; B65D 41/0435; B65D 41/045; B65D 41/20
See application file for complete search history.

(56) References Cited

U.S. PATENT DOCUMENTS

| | | |
|---|---|---|
| 9,823,261 B2 | 11/2017 | Brennan et al. |
| 10,829,278 B2* | 11/2020 | Kegelman ................ B65D 1/04 |
| 2002/0079284 A1 | 6/2002 | Carano |
| 2003/0155321 A1 | 8/2003 | Bauer et al. |
| 2006/0124578 A1 | 6/2006 | Yousif et al. |
| 2006/0151415 A1* | 7/2006 | Smelko ................... B32B 15/08 |
| | | 215/232 |
| 2010/0233035 A1 | 9/2010 | Denawa et al. |
| 2011/0120998 A1 | 5/2011 | Brauer |
| 2014/0053662 A9 | 2/2014 | Kacian |
| 2016/0167848 A1* | 6/2016 | Koschinat ............... B32B 37/00 |
| | | 435/7.92 |
| 2019/0145996 A1 | 5/2019 | Gebrian et al. |

FOREIGN PATENT DOCUMENTS

| | | |
|---|---|---|
| EP | 2 644 273 A2 | 10/2013 |
| JP | H04-072193 A | 3/1992 |
| JP | H05-196560 A | 8/1993 |
| JP | 2000-131326 A | 5/2000 |
| JP | 2013-066916 A | 4/2013 |
| JP | 2015-114222 A | 6/2015 |
| WO | 2014/134331 A1 | 9/2014 |
| WO | 2015/069546 A2 | 5/2015 |

OTHER PUBLICATIONS

'Nylon or Polypropylene in Synthetic Turf' (Zeager Bros Inc) Apr. 17, 2016. Retrieved from the Internet on Aug. 24, 2017. URL: <http://www.zeager.com/content/uploads/2016/04/Nylon-vs-PE-Products.pdf>.
Extended EP Search Report dated Apr. 3, 2019 of corresponding European Application No. 17820967.2, 4 Pages.
Pan Weisan: "Industrial Pharmacy"; China Medical Science and Technology Press; CN; Aug. 31, 2015; pp. 518-522; ISBN 978-7-5067-7400-0 / Aug. 31, 2015.
Luo Guanglin: "Printing Packaging Materials" China Light Industry Press; Yinshu Baozhuang Cailiao; CN; Mar. 31, 2002; pp. 356-360; ISBN 7-5019-3616-1 / Mar. 31, 2002.

* cited by examiner

CAP AND INDUCTION SEAL DESIGNED TO BE OPENED BY PIERCING IN A DIAGNOSTIC ANALYZER

CROSS-REFERENCE TO RELATED APPLICATIONS

This application claims priority to U.S. provisional application Ser. No. 62/357,911 filed Jul. 1, 2016, the contents of which is incorporated herein by reference in its entirety.

TECHNOLOGY FIELD

The present invention relates generally to a cap and a seal for a container in use in a diagnostic analyzer, and more particularly to an induction-sealed container with a removable cap to conceal a mouth of a reagent container used in a diagnostic analyzer.

BACKGROUND

Caps, in particular injection-molded screw caps, are commonly used for sealing containers, such as bottles. A primary function of caps is to keep a container closed and leak-free until contents of the container are to be used.

Screw caps are known to operate acceptably when installed on containers that are sealed by an induction-sealed membrane. Inside of such caps an "energy director" projector may be included to apply pressure to a contact area of a top throat surface of a container and a heat bonding layer of the membrane. Such a membrane may include an aluminum foil layer between two polymeric layers, such as polyethylene and polypropylene. A bottom polymer layer is sealed to an opening of the container by inductive heating of the aluminum foil layer, thereby melting and bonding the bottom polymer layer to the container. The seal serves to protect the contents of the container, and form a leak-proof closure of the container. Access to the container contents is performed by removal of the cap and manual peeling or perforation of the induction-sealed membrane.

However, when used in an automatic process that requires a high throughput, such as a diagnostic analyzer, manual removal of the cap and peeling/perforation of the membrane is undesirable due to the amount of required operator-incurred time and the opportunity for introducing cross-contaminants. Thus, there is a need for providing access to contents of a container in an automated manner in a diagnostic analyzer, while reducing possibilities for cross-contamination and spillage.

SUMMARY

Embodiments are directed to a removable cap with a top hole and a seal with a heat induction closure for sealing an opening of a container.

In an embodiment, an apparatus to cover a reagent container used in a diagnostic analyzer in an in vitro diagnostics (IVD) environment comprises: a cap comprising a sidewall and a top wall with an open access hole on and through the top wall, the cap configured to be attached to a throat of the reagent container, the throat comprising an opening; and an induction seal for sealing the opening of the throat of the reagent container. The induction seal comprises: a first polymer sealing layer configured to be heat-sealed to an outer surface of the opening of the throat of the reagent container; an aluminum foil layer arranged on top of the first polymer sealing layer and configured to heat seal the first polymer sealing layer by inductive heating to the outer surface of the opening of the throat of the reagent container; and a second polymer layer arranged on top of the aluminum foil layer and configured to protect the aluminum foil layer and the first polymer layer. The induction seal is accessible through the open access hole of the cap and is configured to be opened by a perforation device and hold an opened shape when perforated, while remaining adhered to the outer surface of the opening of the throat of the reagent container.

According to another embodiment, an apparatus for storing one or more fluids in a diagnostic analyzer in an in vitro diagnostics (IVD) environment comprises: a container comprising one or more storage portions, each storage portion comprising a throat with a throat sidewall, an opening, and an outer surface of the opening; one or more caps, each cap comprising a sidewall and a top wall with an open access hole on and through the top wall, the cap configured to be attached to the throat of the storage portion of the container; and one or more induction seals, each of the one or more induction seals corresponding to a respective pair of one of the one or more caps and one of the one or more storage portions, for sealing the opening of the throat of the storage portion of the container. Each induction seal comprises: a first polymer sealing layer configured to be heat-sealed to an outer surface of the opening of the throat of the storage portion; an aluminum foil layer arranged on top of the first polymer sealing layer and configured to heat seal the first polymer sealing layer by inductive heating to the outer surface of the opening of the throat of the storage portion; and a second polymer layer arranged on top of the aluminum foil layer and configured to protect the aluminum foil layer and the first polymer layer. The induction seal is accessible through the open access hole of the cap and is configured to be opened by a perforation device and hold an opened shape when perforated, while remaining adhered to the outer surface of the opening of the throat of the storage portion.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

Embodiments are directed to a removable cap with a top hole and a seal with a heat induction closure for sealing an opening of a container. Advantageously, according to embodiments provided herein, the cap and the seal do not need to be removed for a probe to access contents of the container, when used in a diagnostic analyzer, thereby eliminating operator steps of cap removal and seal peeling or perforation. According to embodiments, automated opening of the cap and seal combination is provided by puncturing the seal without removal of the cap from the container. The seal advantageously retains its opened shape required for unobstructed, non-contact probe access to contents of the container. Cross-contamination and level sense problems are addressed by prevention of unintended probe contact with surfaces other than the container's contents.

Although embodiments are described with respect to a reagent container for use in a diagnostic or clinical analyzer, the invention is not so limited. The cap and the seal provided herein may be used in any type of environment in which it is desired to open a seal on a container for access to contents contained in the container.

Figure 1:
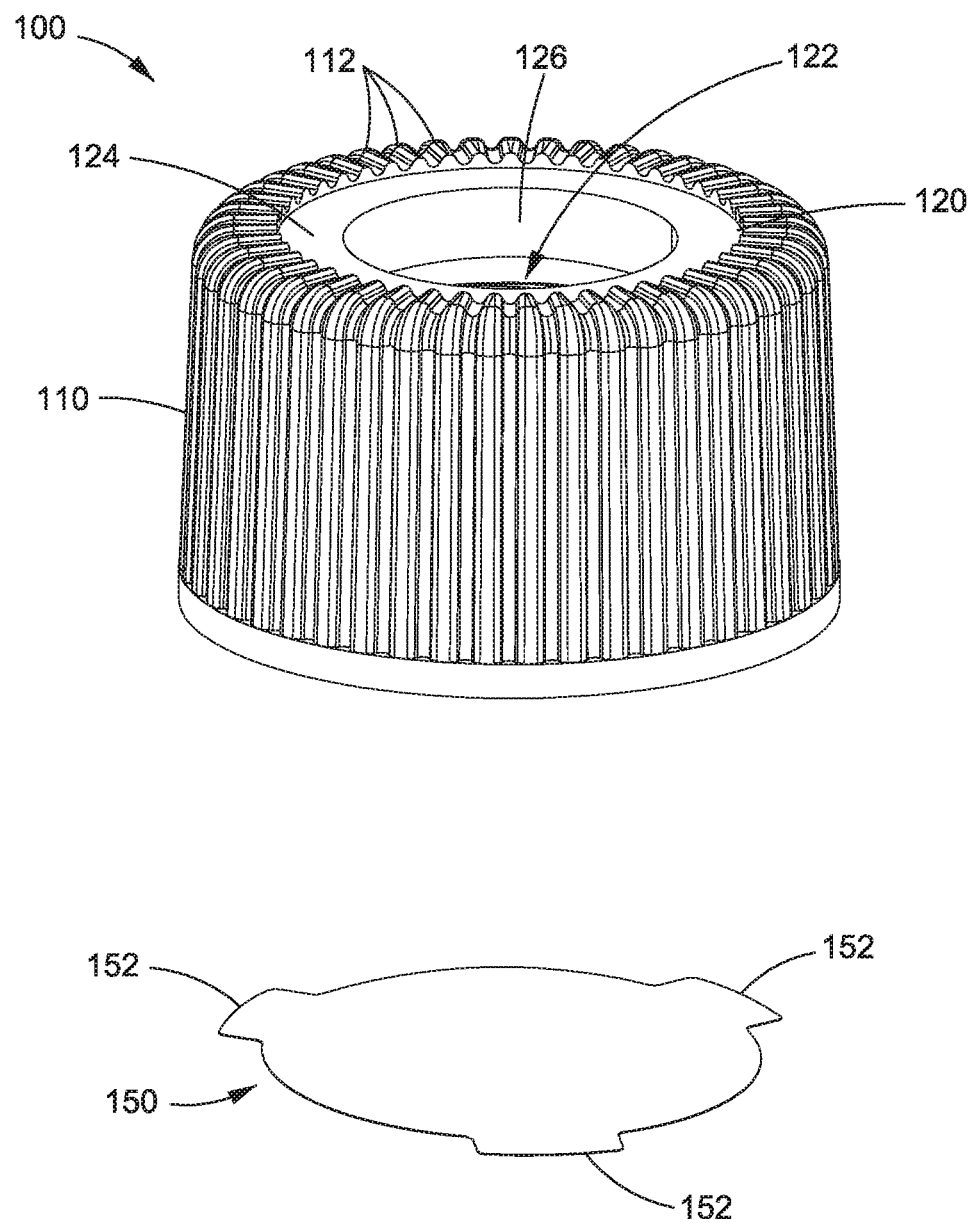
FIGS. 1 and 2 are diagrams depicting views of a cap and a seal, according to an embodiment.
Figure 2:
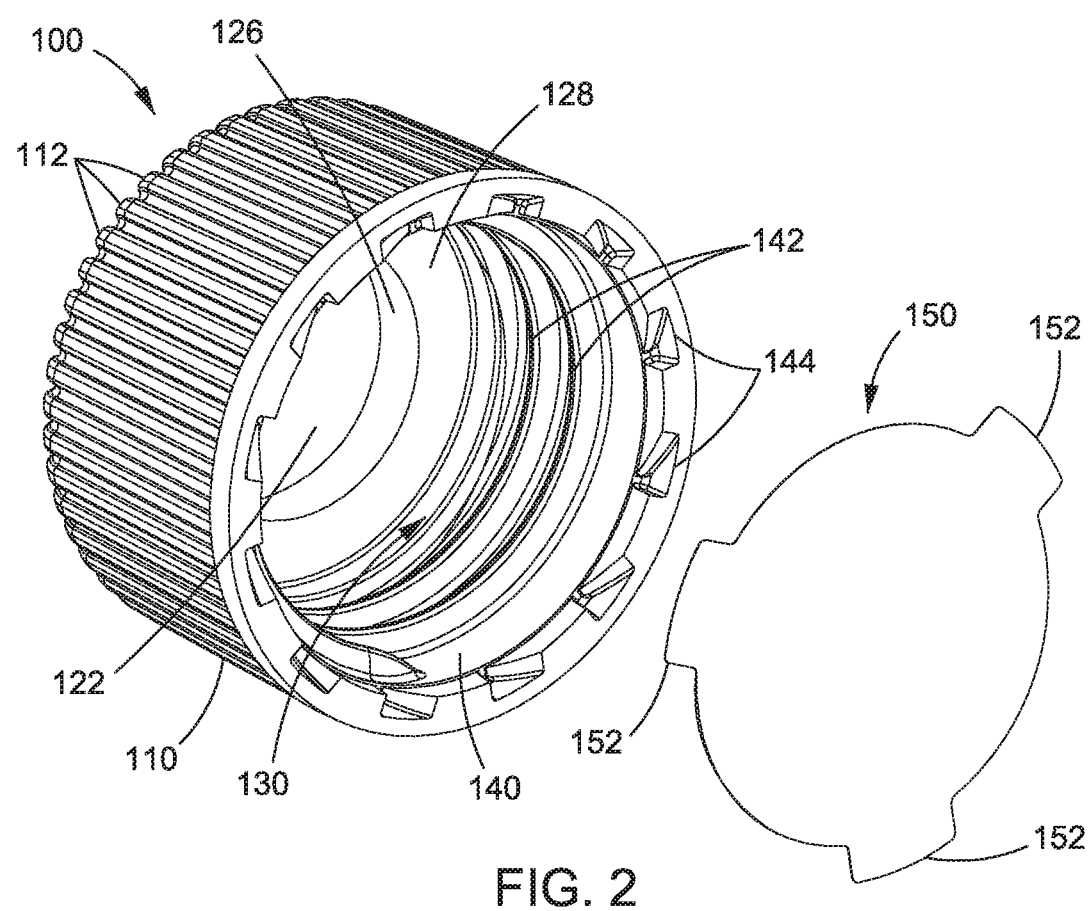

With reference to FIGS. 1 and 2, features of a cap 100 and a seal 150 are illustrated, according to an embodiment. FIG. 1 is a top perspective view of the cap 100 and the seal 150, and FIG. 2 provides an underside perspective view of the cap 100 and the seal 150.

The cap 100 is comprised of a sidewall 110 and a top wall 120. The sidewall 110 and the top wall 120 define an interior portion 130 (see FIG. 2) of the cap 100.

The sidewall 110 and a portion of the top wall 120 may, as shown in the embodiment of FIGS. 1 and 2, have a series of ridges 112 on its outer surface to aid in gripping the cap 100. The cap 100 is not limited to this configuration, and the sidewall 110 and/or the top wall 120 may instead have a smooth outer surface or other surface texture.

With continued reference to FIGS. 1 and 2, an open access hole 122 is formed in and through the top wall 120 of the cap 100. In an embodiment, the open access hole 122 is a center hole in the top wall 120. A portion of the top wall 120 surrounding the open access hole 122 is comprised of an upper flat portion 124 (see FIG. 1), a hole sidewall 126 (see FIGS. 1 and 2), and a bottom projector 128 (see FIG. 2).

As shown in FIG. 2, an internal sidewall 140 of the cap 100 may include threads 142 and/or one or more tabs 144 for connection of the cap 100 to a container, as described below. The cap 100 is not limited to such a configuration of the internal sidewall 140, and other designs may instead be utilized, such as, for example, an internal sidewall 140 with components for snap-fitting the cap 100 onto a container.

In an embodiment, the cap 100 is formed of polypropylene, such as a high-density polypropylene, although the cap 100 is not so limited.

As shown in FIGS. 1 and 2, the seal 150 is of a generally circular shape with one or more projecting tabs 152. The tabs 152 may be of a generally square or rectangular shape, although in other embodiments other shapes (e.g., triangular) may be utilized. In an embodiment, the tabs 152 are not included. In such an embodiment, the circular shape of the seal 150 may be of a larger diameter to accommodate fitting on a container.

Figure 3:
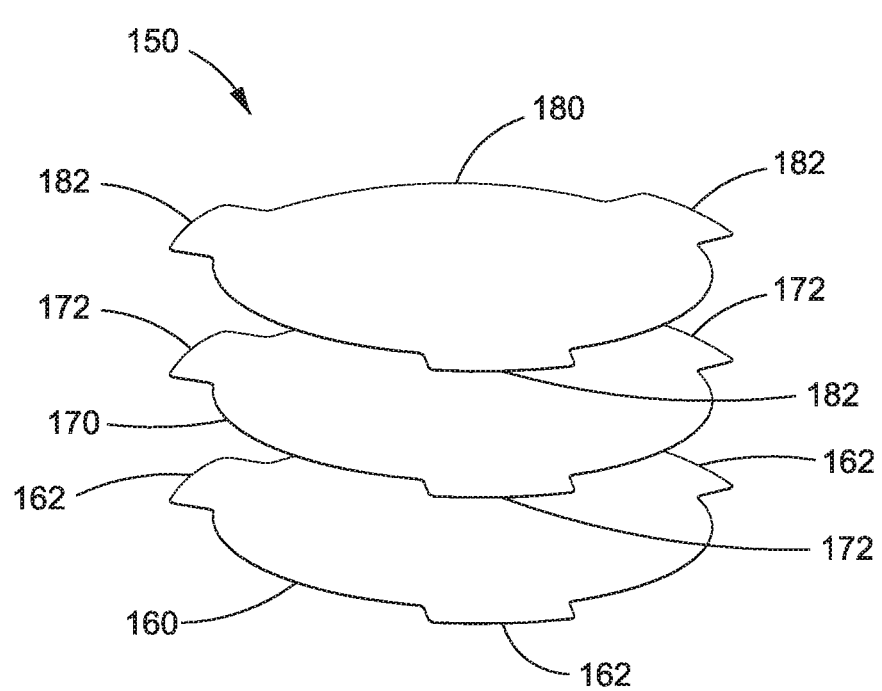
FIG. 3 is a diagram illustrating aspects of a multi-layer seal, according to an embodiment.

FIG. 3 is a diagram illustrating additional aspects of the seal 150, according to an embodiment. The seal 150, according to an embodiment, is comprised of three layers: a first (bottom) polymer sealing layer 160 comprising a heat-sealable polymer capable of being heat-sealed to a container; an aluminum foil (middle) layer 170 arranged on top of the first polymer sealing layer 160, comprising aluminum foil to heat seal the first polymer sealing layer 160 by inductive heating of the aluminum; and a second (top) polymer layer 180 arranged on top of the aluminum foil layer 170 configured to protect the aluminum foil layer 170 and the first polymer sealing layer 160.

Each of the layers 160, 170, and 180 may have one or more projecting tabs, respectively 162, 172, and 182.

In an embodiment, the first polymer sealing layer 160 comprises polyethylene, and the second polymer layer 180 comprises polyethylene terephthalate. In an embodiment, the second polymer layer 180 comprising polyethylene terephthalate forms a laminate with the aluminum foil layer 170.

Figure 4:
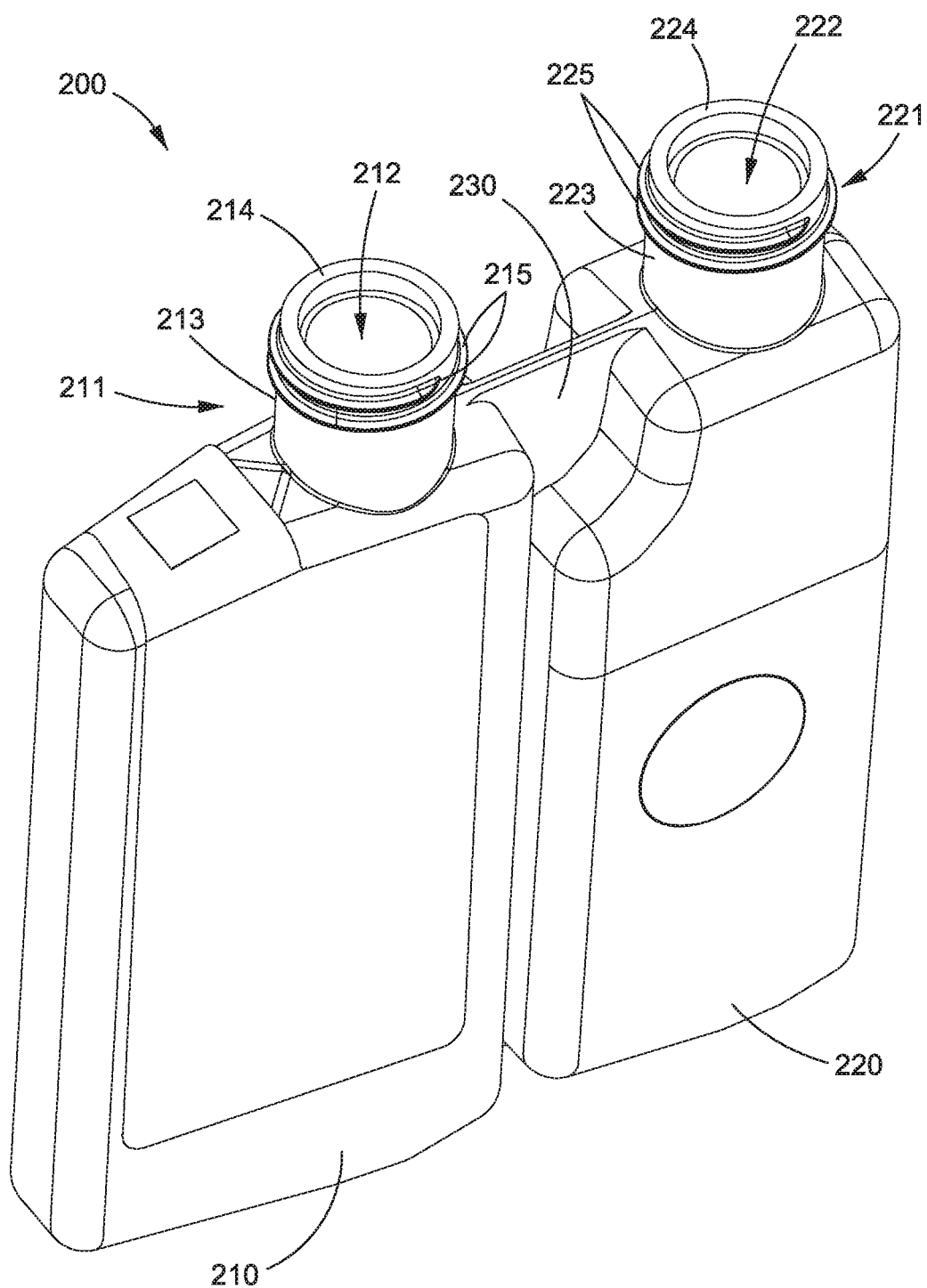
FIG. 4 is a diagram of an exemplary container, according to an embodiment.

FIG. 4 is a diagram of an exemplary container 200 that may be used with the cap 100 and the seal 150. Other types of containers or variations of the container 200 may be used, and the cap 100 and the seal 150 are not limited to use of the exemplary container 200 described herein. Detailed features of an exemplary reagent container are provided in PCT Patent Application Serial No. PCT/US14/019078, the contents of which are hereby included by reference in their entirety herein.

According to an embodiment, as shown in FIG. 4, the container 200 is comprised of two storage portions (or packs) 210, 220 configured to hold fluids (e.g., reagent fluids) or other materials (e.g., powders) for a particular on-board diagnostic test on a diagnostic analyzer, for example. A gripping portion 230 may extend between the two storage packs 210, 220 and is, in an embodiment, a substantially flat surface that may have one or more protrusions or gripping portions provided thereon.

Each storage portion 210, 220 comprises a throat 211, 221, respectively, to which a cap 100 and a seal 150 may be attached, according to embodiments provided herein. The throat 211 comprises an opening 212, a throat sidewall 213, and a top surface 214 of the throat sidewall 213 (i.e., an outer surface of the opening 212). Throat sidewall threads 215 may be formed on the throat sidewall 213 for mating with the threads 142 of the internal sidewall 140 of the cap 100. As noted above, the container 200 and the cap 100 are not limited to the threaded configuration and each may instead have other components or characteristics for mating together the cap 100 and the container 200 (e.g., snap-fit components or the like). Similar to the throat 211, the throat 221 comprises an opening 222, a throat sidewall 223, and a top surface 224 of the throat sidewall 223 (i.e., an outer surface of the opening 222). Throat sidewall threads 225 may be formed on the throat sidewall 223 for mating with the threads 142 of the internal sidewall 140 of the cap 100.

Of course, the container 200 shown in and described herein with reference to FIG. 4 is purely exemplary and non-limiting to the cap 100 and the seal 150 disclosed herein. In an embodiment, a container to be used with the cap 100 and the seal 150, according to embodiments provided herein, may have a single storage portion, for example. Moreover, the container 200, or variations thereof, is not required to be used to store reagent fluids for use in a diagnostic analyzer.

Figure 5:
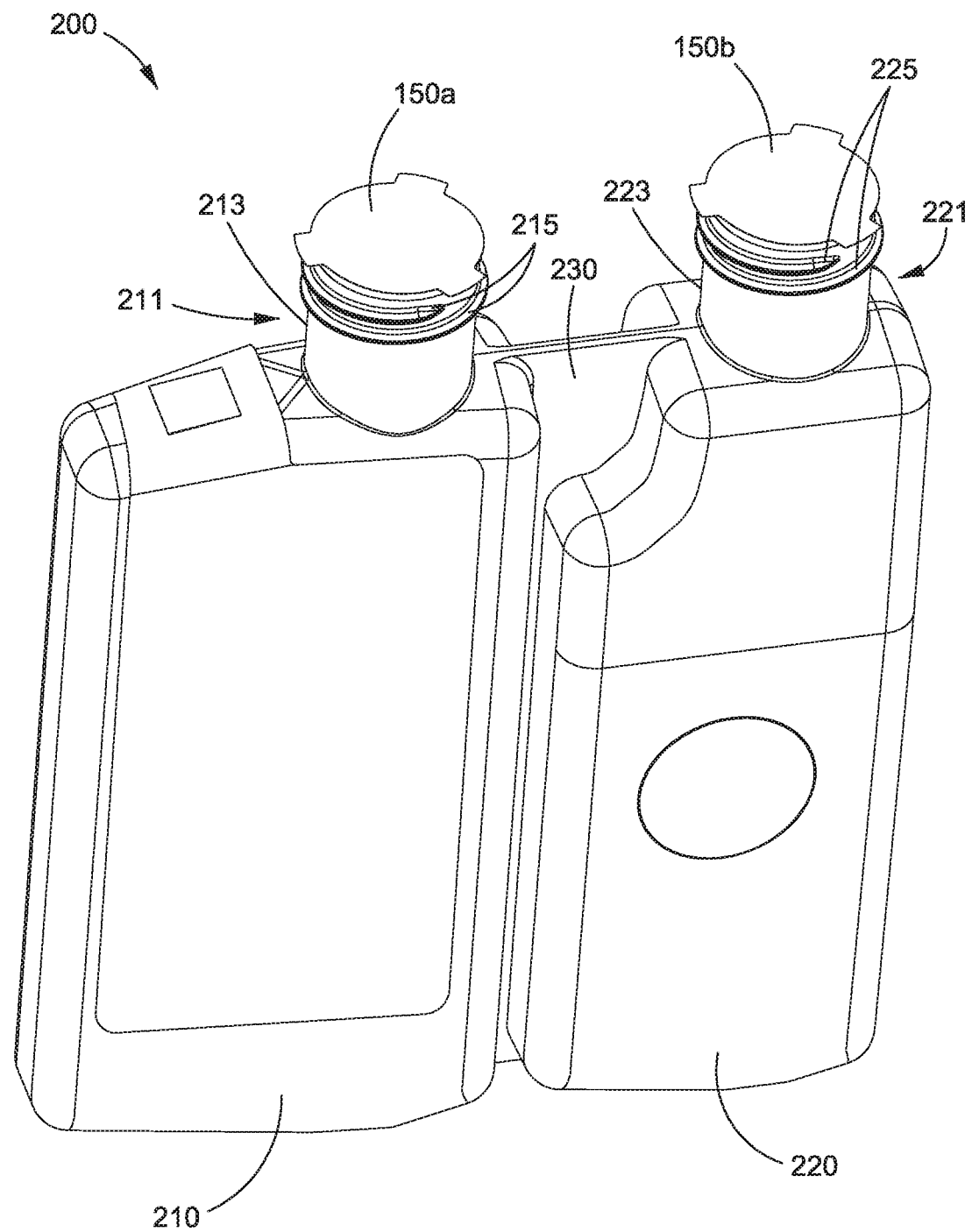
FIG. 5 illustrates an exemplary container with seals covering openings of the container, according to an embodiment.

FIG. 5 depicts an exemplary container 200 with seals 150a, 150b sealed to the top surfaces 214, 224 of the throat sidewalls 213, 223 to cover the openings 212, 222, respectively, according to an embodiment.

Figure 6:
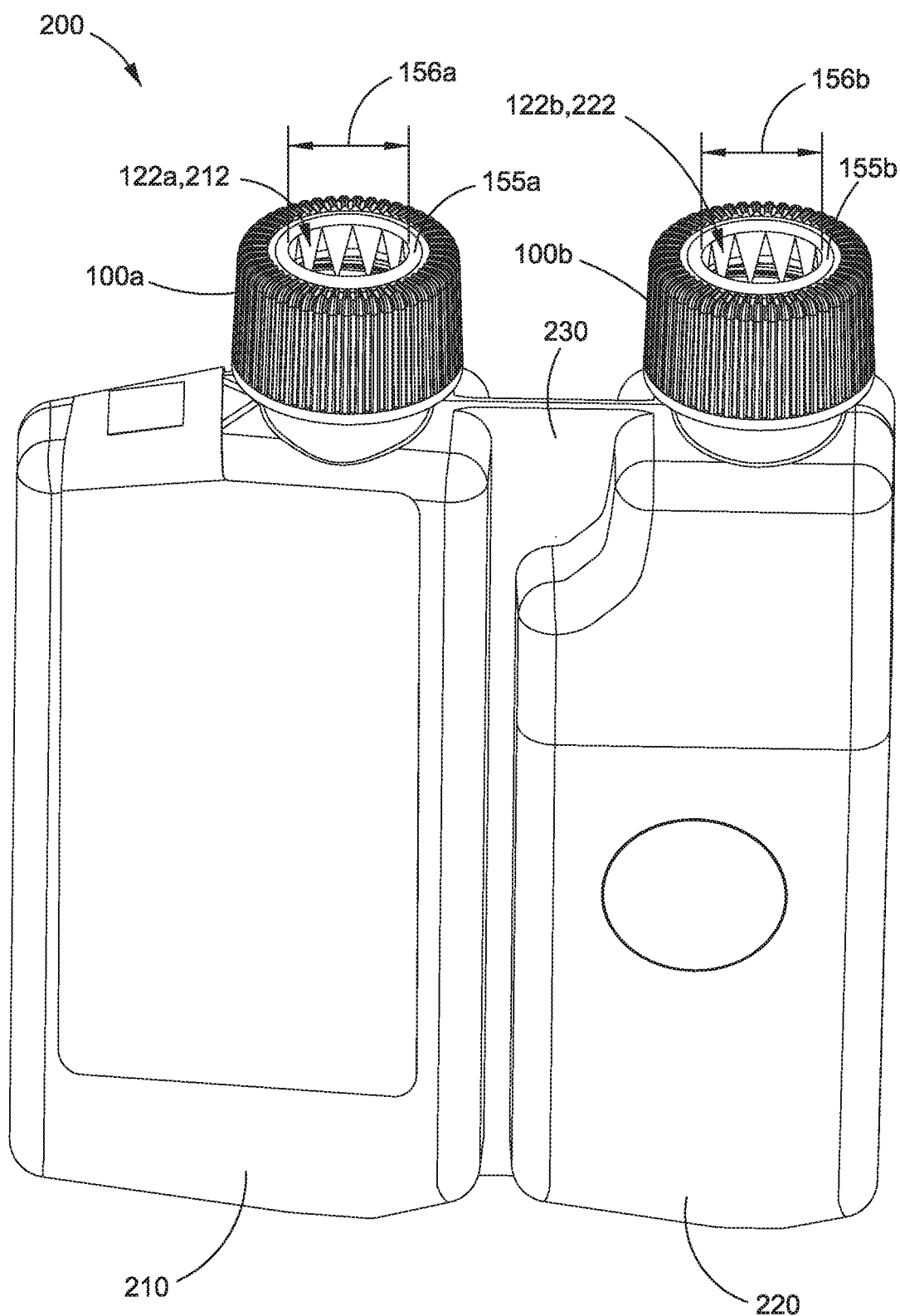
FIG. 6 illustrates an exemplary container with caps and seals attached thereto with the seals punctured, according to an embodiment.

FIG. 6 illustrates an exemplary container 200 with caps 100a, 100b attached to the throats 211, 221 and with punctured seals 155a, 155b sealed to the top surfaces 214, 224 of the throat sidewalls 213, 223 to cover the openings 212, 222, respectively, according to an embodiment. As shown in FIG. 6, the punctured seals 155a, 155b (seals 150a, 150b punctured via a puncturing tool) provide access via openings 156a, 156b of the punctured seals 155a, 155b to contents of the container 200. As shown, the openings 212, 222 of the container 200 are accessible via the openings 156a, 156b of the punctured seals 155a, 155b through the open access holes 122a, 122b of the caps 100a, 100b.

Figure 7:
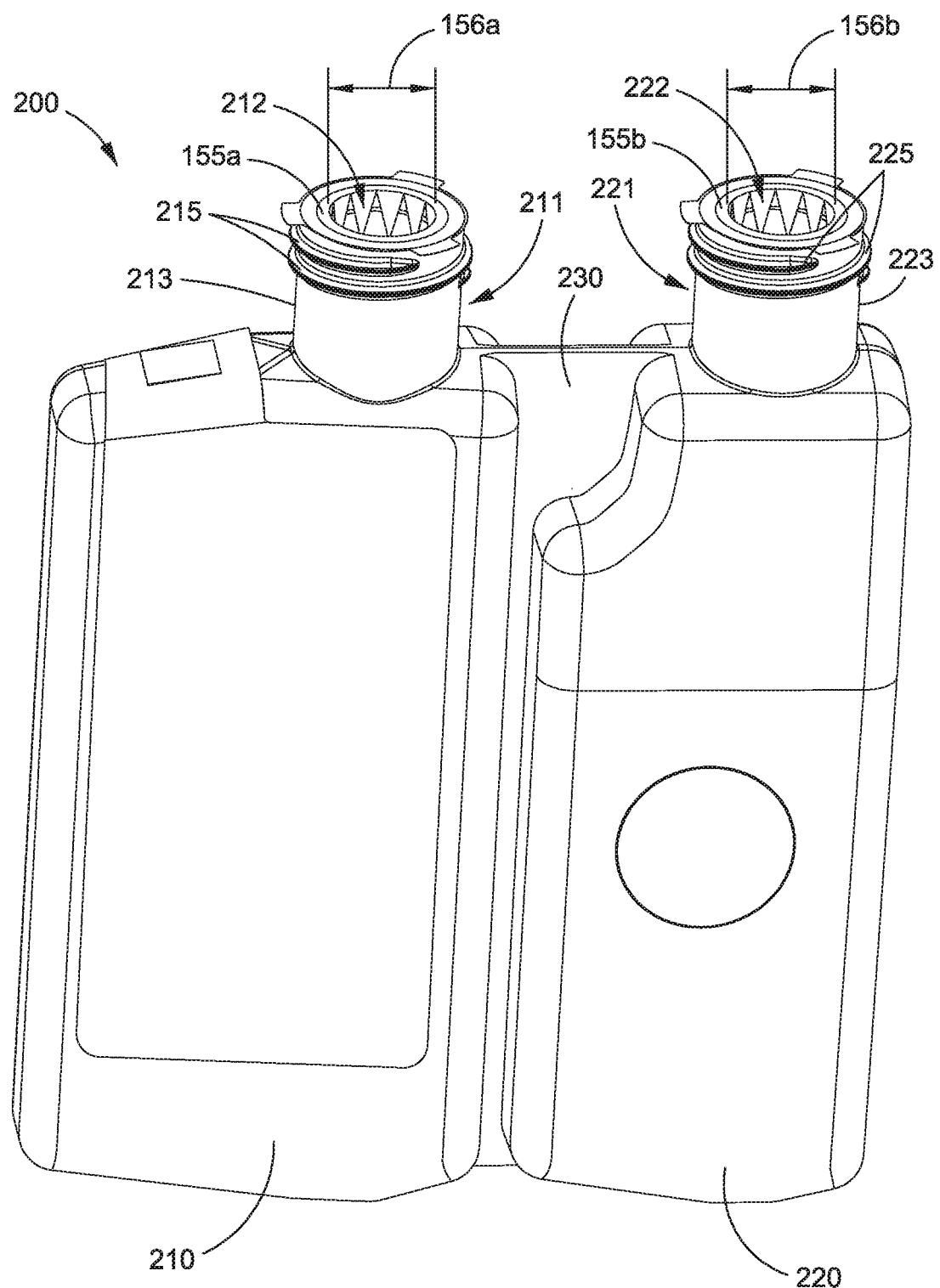
FIG. 7 illustrates an exemplary container with seals attached thereto and with the seals punctured, according to an embodiment.

FIG. 7 provides a view of an exemplary container 200 with punctured seals 155a, 155b attached thereto, with the caps 100a, 100b removed, according to an embodiment.

According to embodiments herein, the first polymer sealing layer 160 performs a seal adhesion function by application of heat energy (from induction heating of the aluminum foil layer 170) and contact pressure (from the cap 100, and in particular the bottom projector 128 of the cap 100 which holds in place the seal 150 within the cap 100 between the cap 100 and the top surface 214, 224 of the throat 211, 221 of the container 200 during the sealing process) to result in a molecular bonding of the first polymer sealing layer 160 and the container 200 due to the matching material compositions of the first polymer sealing layer 160 and the container 200.

According to embodiments herein, the aluminum foil layer 170 performs the following functions: transfer of induced heat to the polyethylene first polymer sealing layer 160 and the second polymer layer 180, for molecular thermal seal bonding of the first polymer sealing layer 160 to a top surface 214, 224 of the throat 211, 221 of the container 200; and the formable and "memory" shaping characteristics of the aluminum foil layer 170 introduce shape retention capability and thus the ability to "hold open" the first polymer sealing layer 160 and the second polymer layer 180.

According to an embodiment, the second polymer layer 180 is exposed to the external environment surrounding the cap 100, the seal 150, and the container 200, thus providing a protective layer for the first polymer sealing layer 160 and the aluminum foil layer 170 from degradation related to ambient or external exposure to contamination. As such, the second polymer layer 180 is an ambient, vapor, and waterproof seal.

According to an embodiment, the thermal-induced adhesion (i.e., holding) power of the first polymer sealing layer 160 to the container 200 is greater than that of the peel force between that of the first layer 160 to the second layer 170 and the second layer 170 to the third layer 180.

In an embodiment, a holding power of the first polymer sealing layer 160 is greater than a required shear force to perforate the aluminum foil layer 170 and the second polymer layer 180.

According to an embodiment, the second polymer layer 180 is comprised of a dissimilar material to the cap 100. In an embodiment, the second polymer layer 180 and the cap 100 have a difference in releasing power to the first polymer sealing layer 160 to the container 200 based on the differences in their respective materials. The difference in materials between the cap 100, the foil layer 170, and the polymer seal layers 160, 180 isolates the cap 100, preventing induction process adhesion of the cap 100 to the seal 150.

In an embodiment, a melting temperature of the first polymer sealing layer 160 is lower than a melting temperature of the second polymer layer 180.

As shown in FIG. 7, removal of the caps 100a, 100b from the container 200 does not result in damage to or otherwise affects the punctured seals 155a, 155b, thus leakage due to loosening of the cap 100a, 100b is prevented and the seals 150a, 150b or punctured seals 155a, 155b remain adhered to the container 200. As a consequence of the puncturing of the seals 150a, 150b, full open access to the contents of the container 200 is achieved without probe or instrument contact to the punctured seals 155a, 155b.

According to an embodiment, a seal 150 is placed within an interior portion 130 of a cap 100. The cap 100 is attached to the throat 211, 221 of the container 200, and the cap 100 and the seal 150 are thus, via the projector 128 of the cap 100, in contact with the top surface 214, 224 of the throat sidewall 213, 223 (i.e., an outer surface of the opening 212, 222). The cap 100 and the seal 150 are exposed to an induction heat source, according to methods known to those of ordinary skill in the art. The aluminum foil layer 170 of the seal 150 transfers heat to the first polymer sealing layer 160 to bond the seal 150 to the top surface 214, 224 of the throat sidewall 213, 223 of the container 200. According to an embodiment, the heat induction is such that the attachment of the first polymer sealing layer 160 is contiguous and without void, so that the first polymer sealing layer 160 is molecularly bonded from both surfaces (i.e., the top surface 214, 224 of the container throat 211, 221 and the underside of the first polymer sealing layer 160). The application of heat to the aluminum foil layer 170 causes the polymer surface of the layer 160 to melt and results in molecular bonding of the polypropylene seal layer 160 to the polypropylene container throat top surface 214, 224. Removal of the cap 100 after heat induction will not void or compromise the sealed surface of the container 200 and a sealed closure will remain until it is pierced or punctured by a puncturing device. The piercing of the seal 150 by penetration of an opener tool or puncturing device produces an underside curl-shaping of the seal 150 (i.e., punctured seal 155a, 155b as shown in FIGS. 6 and 7), which remains open due to the tension of the aluminum foil layer 170 of the seal laminate. The piercing or puncturing of the seal 150 may be done by automation, but may also be accomplished manually with a hand-tool used by an operator.

According to an embodiment herein, removal of the cap 100 is unnecessary to penetrate the seal 150, and once perforation has been carried out, the aluminum foil layer 170 retains the punctured shape of the opening 156 to provide continued access to the contents of the container 200. The penetration of the seal 150 results in formation and control of the sizing of the punctured seal opening 156. Limited only by the size of the open access hole 122, the curled access flanges (i.e., the opening 156 of the punctured seal 155) then become a physical method to retain the opening and prevent probe or other instrument contact to the punctured seal 155 (e.g., in an embodiment, the open access hole 122 comprises a 9.1 mm opening, compared to a 1.5 mm diameter of a probe). The projections of aluminum maintain the parting of the seal 150 and prevent retraction or re-closure of the punctured seal opening 156, thereby eliminating contact contamination of the probe to aspirations and atomization particulates deposited upon the seal 150. The seal 150 remains attached to the container throat top surface 214, 224, and remains intact even in the event that the cap 100 is removed. Repeat probe access to the container 200, including the emptying of the container 200, is provided without interference of the seal 150 to the accessing probe.

The combination of the cap 100 and the seal 150 to cover a container 200 and provide access to contents contained therein, as disclosed herein, has several advantages: the seal 150 protects contents from waste and spillage; operator spills are reduced; incidents of contamination are reduced; ease-of-use and operability are increased. Additionally, instrument errors from probe contact with unintended contamination is prevented, resulting in increased reliability and performance to customers. In a diagnostic analyzer embodiment, in which the container 200 is used for reagents, automated opening and preparation of the container seal 150 for a reagent probe adds value to the instrument performance during reagent probe single or full cycle loading by forming a large access target free of seal obstruction (i.e., the punctured seal opening 156a, 156b). Non-utilization hours observed from probe contact with seal material is eliminated. Customer profits are increased due to the increased reliability of reagent probe access and elimination of current extensive operator time.

Figure 8:
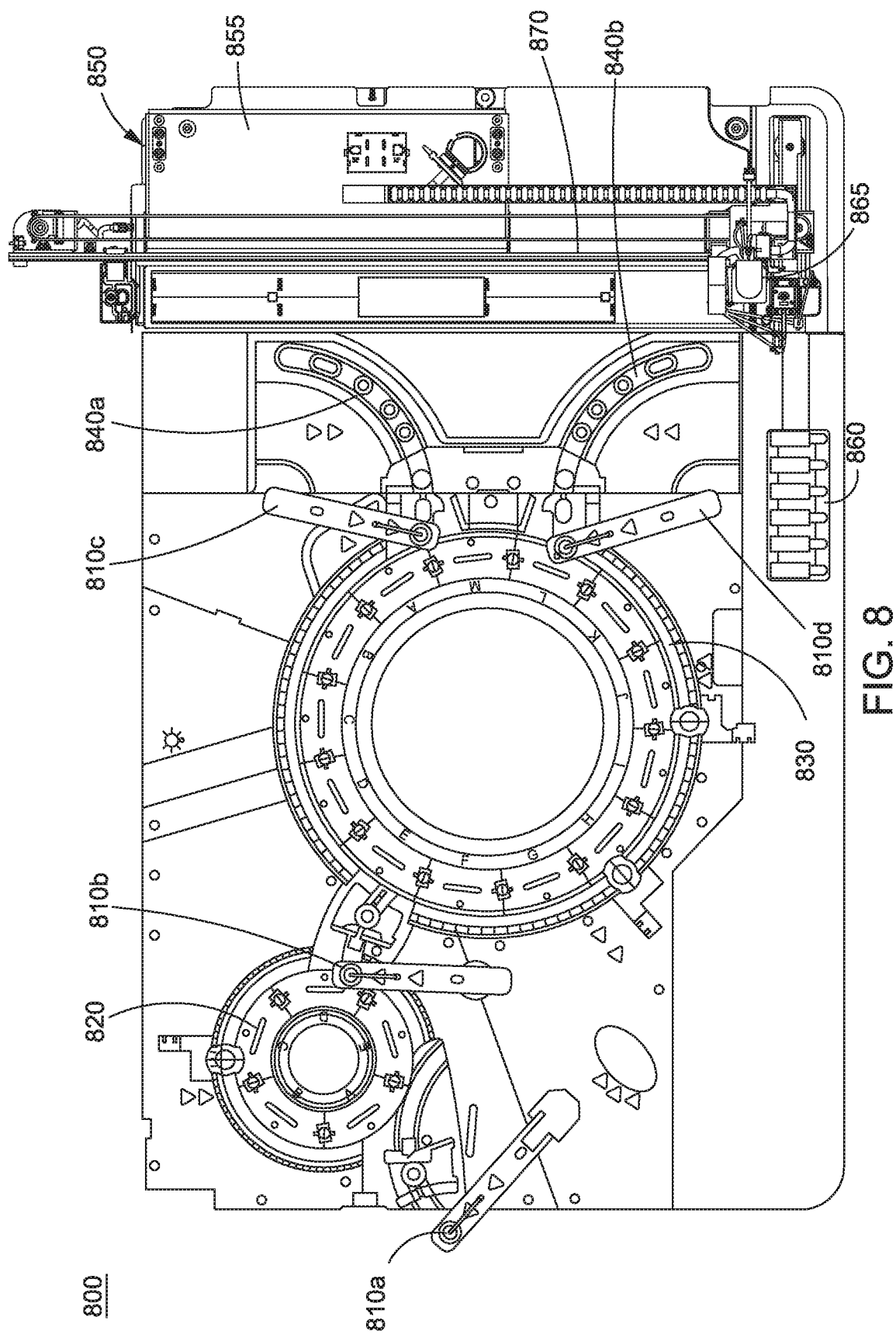
FIG. 8 is a layout of an example system architecture within which embodiments of the invention may be used, according to an embodiment.

FIG. 8 provides a layout of an example system architecture 800 within which embodiments of the invention may be implemented, according to an embodiment. Shown in FIG. 8 are various transfer arms 810 (810a, 810b, 810c, and 810d) with respective probes; a diluting turntable 820 including a plurality of diluting containers arranged in one or more diluting rings; a reaction turntable 830 including a plurality of reaction containers arranged in one or more reaction rings; and reagent storage areas 840a and 840b dedicated to storage and supply of a respective reagent, each reagent storage area 840a and 840b including space for a plurality of reagent containers. In operation, transfer arm 810a and its respective probe may operate to transfer sample from an access position to one or more diluting containers on the diluting turntable 820 to create a dilution therein. Transfer arm 810b and its respective probe may operate to transfer dilution from a diluting container to a reaction container on the reaction turntable 830. Transfer arms 810c and 810d and their respective probes may operate to transfer a reagent from reagent storage area 840a and 840b, respectively, to a reaction container on the reaction turntable 830. The various transfers occur by use of a pumping mechanism (not shown), such as a displacement pump, for example, attached to the transfer arms 810. Additionally, the system architecture 800 includes one or more controllers (not shown) for controlling operation of the various components, including the transfer arms 810, the probes, and the turntables.

Also included in the system architecture 800 is a reagent handling system 850 for transferring one or more of the containers 200 to and/or from the reagent storage areas 840a and 840b. The reagent handling system 850, according to an embodiment, includes a reagent server module 855, which is, in an embodiment, a refrigerated storage enclosure comprising one or more indexing rings for storing reagent containers 200.

A tray 860 is configured to hold one or more containers 200 for transfer to and from the reagent server module 855. The tray 860 is accessible to an operator for manual loading and unloading of containers 200 to and from the tray 860, which may move on a track.

A gripper assembly 865, in an embodiment, is provided to automatically transfer containers 200 (with caps 100 and seals 150, according to embodiments disclosed herein) between the tray 860 and the reagent server module 855. The gripper assembly 865 moves along a horizontal transfer arm 870 while gripping a container 200 to transfer the container 200. In an embodiment, the gripper assembly 865 includes a pair of gripper fingers that are oriented vertically and opposite one another for gripping a portion of a container 200 and for puncturing or piercing a seal 150 attached to a container 200 without removal of an attached cap 100.

The system architecture 800 of FIG. 8 and the accompanying description are purely exemplary and non-limiting to the cap 100 and the seal 150 disclosed herein. The system architecture 800 is just one example system in which the cap 100 and the seal 150 may be used.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. An apparatus to cover a reagent container used in a diagnostic analyzer in an in vitro diagnostics (IVD) environment, the apparatus comprising:
    a cap comprising a sidewall and a top wall with an open access hole on and through the top wall, the cap configured to be attached to a throat of the reagent container, the throat comprising an opening; and
    an induction seal for sealing the opening of the throat of the reagent container, the induction seal comprising:
        a first polymer sealing layer configured to be heat-sealed to an outer surface of the opening of the throat of the reagent container;
        an aluminum foil layer arranged on top of the first polymer sealing layer and configured to heat seal the first polymer sealing layer by inductive heating to the outer surface of the opening of the throat of the reagent container; and
        a second polymer layer arranged on top of the aluminum foil layer and configured to protect the aluminum foil layer and the first polymer layer, and
        wherein a thermal-induced adhesion power of the first polymer sealing layer to the reagent container is greater than that of a peel force between that of the first polymer sealing layer to the aluminum foil layer and the aluminum foil layer to the second polymer layer; and
    wherein the induction seal is accessible through the open access hole of the cap and is configured to be opened by a perforation device traveling through the open access hole of the cap and hold an opened shape when perforated, while remaining adhered to the outer surface of the opening of the throat of the reagent container.

2. The apparatus of claim 1, wherein the aluminum foil layer transfers induced heat to the first polymer sealing layer and the second polymer layer for molecular thermal seal bonding of the first polymer sealing layer to the outer surface of the opening of the throat of the reagent container; and wherein physical properties of the aluminum foil layer provide for the first polymer sealing layer and the second polymer layer to retain the opened shape when perforated.

3. The apparatus of claim 1, wherein the first polymer sealing layer comprises polyethylene.

4. The apparatus of claim 1, wherein the second polymer layer comprises polyethylene terephthalate.

5. The apparatus of claim 1, wherein the cap comprises one of a screw-on cap or a snap-on cap.

6. The apparatus of claim 1, wherein a holding power of the first polymer sealing layer is greater than a shear force required to perforate the aluminum foil layer and the second polymer layer.

7. The apparatus of claim 1, wherein the second polymer layer is comprised of a dissimilar material to the cap, wherein the second polymer layer and the cap have a difference in releasing power to the first polymer sealing layer to the container based on the differences in their respective materials.

8. The apparatus of claim 1, wherein a melting temperature of the first polymer sealing layer is lower than a melting temperature of the second polymer layer.

9. The apparatus of claim 1, wherein a portion of the top wall surrounding the open access hole comprises an upper flat portion, a hole sidewall having a first end and a second end, wherein the hole side wall is connected to the upper flat portion at the first end and vertically extends within an interior portion of the cap, and a bottom projector within an interior portion of the cap connected to the second end of the hole side wall, wherein the bottom projector provides contact pressure to hold in place the seal between the cap and the container during the inductive heating.

10. An apparatus for storing one or more fluids in a diagnostic analyzer in an in vitro diagnostics (IVD) environment, the apparatus comprising:
  a container comprising one or more storage portions, each storage portion comprising a throat with a throat sidewall, an opening, and an outer surface of the opening;
  one or more caps, each cap comprising a sidewall and a top wall with an open access hole on and through the top wall, the cap configured to be attached to the throat of the storage portion of the container; and
  one or more induction seals, each of the one or more induction seals corresponding to a respective pair of one of the one or more caps and one of the one or more storage portions, for sealing the opening of the throat of the storage portion of the container, each induction seal comprising:
    a first polymer sealing layer configured to be heat-sealed to an outer surface of the opening of the throat of the storage portion;
    an aluminum foil layer arranged on top of the first polymer sealing layer and configured to heat seal the first polymer sealing layer by inductive heating to the outer surface of the opening of the throat of the storage portion; and
    a second polymer layer arranged on top of the aluminum foil layer and configured to protect the aluminum foil layer and the first polymer layer, and
    wherein a thermal-induced adhesion power of the first polymer sealing layer to the container is greater than that of a peel force between that of the first polymer sealing layer to the aluminum foil layer and the aluminum foil layer to the second polymer layer; and
  wherein the induction seal is accessible through the open access hole of the cap and is configured to be opened by a perforation device traveling through the open access hole of the cap and hold an opened shape when perforated, while remaining adhered to the outer surface of the opening of the throat of the storage portion.

11. The apparatus of claim 10, wherein the throat further comprises throat sidewall threads formed on the throat sidewall, wherein the cap further comprises cap threads formed on an internal sidewall thereof, wherein the throat sidewall threads and the cap threads are configured to mate with one another to attach the cap to the throat of the storage portion of the container.

12. The apparatus of claim 10, wherein contents of each of the one or more storage portions is accessible through the open access hole of the cap and the perforated induction seal, without removal of the cap.

13. The apparatus of claim 10, wherein the aluminum foil layer transfers induced heat to the first polymer sealing layer and the second polymer layer for molecular thermal seal bonding of the first polymer sealing layer to the outer surface of the opening of the throat of the storage portion; and wherein physical properties of the aluminum foil layer provide for the first polymer sealing layer and the second polymer layer to retain the opened shape when perforated, the perforated opening retaining sufficient size to allow reagent probe access with no contact to the first polymer sealing layer.

14. The apparatus of claim 10, wherein a holding power of the first polymer sealing layer is greater than a shear force required to perforate the aluminum foil layer and the second polymer layer.

15. The apparatus of claim 10, wherein the second polymer layer is comprised of a dissimilar material to the cap, wherein the second polymer layer and the cap have a difference in releasing power to the first polymer sealing layer to the container based on the differences in their respective materials.

16. The apparatus of claim 10, wherein a melting temperature of the first polymer sealing layer is lower than a melting temperature of the second polymer layer.

17. The apparatus of claim 10, wherein the first polymer sealing layer comprises polyethylene, and wherein the second polymer layer comprises polyethylene terephthalate.

18. The apparatus of claim 10, wherein a portion of the top wall surrounding the open access hole comprises an upper flat portion, a hole sidewall having a first end and a second end, wherein the hole side wall is connected to the upper flat portion at the first end and vertically extends within an interior portion of the cap, and a bottom projector within an interior portion of the cap connected to the second end of the hole side wall, wherein the bottom projector provides contact pressure to hold in place the seal between the cap and the storage portion of the container during the inductive heating.

* * * * *